United States Patent
Dussarrat et al.

(10) Patent No.: US 9,103,019 B2
(45) Date of Patent: Aug. 11, 2015

(54) METAL PRECURSORS CONTAINING BETA-DIKETIMINATO LIGANDS

(75) Inventors: Christian Dussarrat, Wilmington, DE (US); Benjamin J. Feist, Wilmington, DE (US)

(73) Assignee: American Air Liquide, Inc., Fremont, CA (US)

( * ) Notice: Subject to any disclaimer, the term of this patent is extended or adjusted under 35 U.S.C. 154(b) by 1844 days.

(21) Appl. No.: 12/364,298

(22) Filed: Feb. 2, 2009

(65) Prior Publication Data

US 2009/0197411 A1 Aug. 6, 2009

Related U.S. Application Data

(60) Provisional application No. 61/025,584, filed on Feb. 1, 2008.

(51) Int. Cl.
 *H01L 21/31* (2006.01)
 *C23C 16/18* (2006.01)
 *C07C 251/08* (2006.01)
 *C23C 16/40* (2006.01)
 *H01L 21/3205* (2006.01)

(52) U.S. Cl.
 CPC .............. *C23C 16/18* (2013.01); *C07C 251/08* (2013.01); *C23C 16/406* (2013.01); *H01L 21/32051* (2013.01)

(58) Field of Classification Search
 CPC .................... H01L 21/02274; H01L 21/02126
 USPC ........................................................ 438/778
 See application file for complete search history.

(56) References Cited

U.S. PATENT DOCUMENTS

2006/0292303 A1 * 12/2006 Millward et al. ............. 427/252

OTHER PUBLICATIONS

Lim, B.S. et al. "Atomic layer deposition of transition metals". Nat. Mater. 2003, 2, pp. 749-754.
Lim, B.S. et al. "Synthesis and characterization of volatile, thermally stable, reactive transition metal amidinates". Inorg. Chem. 2003, 42, pp. 7951-7958.
Kim, K. et al. "Characteristics of cobalt thin films deposited by remote plasma ALD method with dicobalt octacarbonyl". J. Electrochem. Soc. 2007, 154, pp. H177-H181.
Zhang, J. et al. "Ethylene polymerization and oligomerization by bulky beta-diketiminato Ni(II) and beta-diimine Ni(II) complexes/methylaluminoxane systems". J. Molecular Catalysis, vol. 249, No. 1-2, Apr. 18, 2006, pp. 1381-1169.
El-Kaderi, H.M. et al. "Sandwich complexes of the heavier alkaline earth metals containing $\eta^5$-beta-diketminato ligand sets". Organometallics 20041011 American Chemical Society, vol. 23, No. 21.
International Search Report and Written Opinion for corresponding PCT/IB2009/050427, Jun. 16, 2009.

* cited by examiner

*Primary Examiner* — Jack Chen
(74) *Attorney, Agent, or Firm* — Patricia E. McQueeney

(57) ABSTRACT

Methods and compositions for depositing a metal containing thin film on a substrate comprises introducing a vapor phase metal-organic precursor into a reaction chamber containing one or more substrates. The precursor has at least one β-diketiminato ligand, and has the general formula:

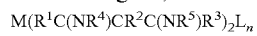

$M(R^1C(NR^4)CR^2C(NR^5)R^3)_2L_n$ wherein M is a metal selected from nickel, cobalt, ruthenium, iridium, palladium, platinum, silver and gold. Each of $R^{1-5}$ is an organic ligand independently selected from H; and a $C_1$-$C_4$ linear or branched, alky group, alkylsilyl group, alkylamide group, alkoxide group, or alkylsilylamide group. Each L is independently selected from: a hydrocarbon; an oxygen-containing hydrocarbon; an amine; a polyamine; a bipyridine; an oxygen containing heterocycle; a nitrogen containing heterocycle; and combinations thereof; and n is an integer ranging from 0 to 4, inclusive.

A metal containing film is deposited onto the substrate, while the substrate is maintained at a temperature between about 100° C. and about 500° C.

8 Claims, No Drawings

METAL PRECURSORS CONTAINING BETA-DIKETIMINATO LIGANDS

CROSS REFERENCE TO RELATED APPLICATIONS

The present application claims the benefit of U.S. Provisional Application Ser. No. 60/61/025,584, filed Feb. 1, 2008, herein incorporated by reference in its entirety for all purposes.

BACKGROUND

1. Field of the Invention

This invention relates generally to compositions, methods and apparatus used for the manufacture semiconductor, photovoltaic, LCF-TFT, or flat panel type devices. More specifically, the invention relates to new precursors for deposition of metal films on to substrates.

2. Background of the Invention

As the design and manufacturing of complementary metal-oxide semiconductors ("CMOS") circuits continues to evolve, the industry is constantly seeking new and novel methods of depositing films onto substrates, such that the resulting film will have certain sought after properties. For example, transition metal thin films may be used as adhesion/seed layers in copper interconnects and as magnetoresistive multilayers in magnetic random access memory devices.

Nickel and cobalt films are desired for future semiconductor devices. In some CMOS architectures NiSi and $CoSi_2$ films may eventually replace the metal gate currently used in conventional transistors. Cobalt silicides may be utilized in device scale-down processes due to their good thermal and chemical stability, low resistivity, wide process window, and the small lattice mismatch to the silicon crystal lattice, which allows the cobalt silicide to be grown epitaxially on the silicon. Furthermore, nickel oxide and cobalt oxide films may be used in the construction of MRAM or FeRAM type devices.

Currently, the main industrial options suitable to deposit such thin films with reasonable throughput and acceptable purity are vapor phase deposition techniques such as chemical vapor deposition ("CVD") and atomic layer depositions ("ALD"). Both of these techniques for depositing a film on a substrate require the use of precursors which are thermally stable, easily vaporized, reactive, and which cleanly decompose.

Consequently, there exists a need for methods and precursors for depositing films containing late transition metal layers.

BRIEF SUMMARY

Embodiments of the present invention provide novel methods and compositions for the deposition of a film on a substrate. In general, the disclosed compositions and methods utilize a precursor compound with at least one β-diketiminato ligand.

In an embodiment, a method for depositing a metal containing thin film on a substrate comprises introducing a vapor phase metal-organic precursor into a reaction chamber containing one or more substrates. The precursor has at least one β-diketiminato ligand, and has the general formula:

wherein M is a metal selected from nickel, cobalt, ruthenium, iridium, palladium, platinum, silver and gold. Each of $R^{1-5}$ is an organic ligand independently selected from H; and a $C_1$-$C_4$ linear or branched, alky group, alkylsilyl group, alkylamide group, alkoxide group, or alkylsilylamide group. Each L is independently selected from: a hydrocarbon; an oxygen-containing hydrocarbon; an amine; a polyamine; a bipyridine; an oxygen containing heterocycle; a nitrogen containing heterocycle; and combinations thereof; and n is an integer ranging from 0 to 4, inclusive.

A metal containing film is deposited onto the substrate, while the substrate is maintained at a temperature between about 100° C. and about 500° C.

In an embodiment, a precursor for depositing a metal containing thin film on a substrate comprises an metal-organic precursor with at least one β-diketiminato ligand, which has the general formula:

wherein M is a metal selected from nickel, cobalt, ruthenium, iridium, palladium, platinum, silver and gold. Each of $R^{1-5}$ is an organic ligand independently selected from H; and a $C_1$-$C_4$ linear or branched, alky group, alkylsilyl group, alkylamide group, alkoxide group, or alkylsilylamide group. Each L is independently selected from: a hydrocarbon; an oxygen-containing hydrocarbon; an amine; a polyamine; a bipyridine; an oxygen containing heterocycle; a nitrogen containing heterocycle; and combinations thereof; and n is an integer ranging from 0 to 4, inclusive.

Other embodiments of the current invention may include, without limitation, one or more of the following features:

- at least one reactant is introduced into the reaction chamber;
- the metal containing film comprises oxygen, and the reactant is at least one member selected from: oxygen; oxygen radicals (e.g. O. or OH.); ozone; nitric oxide; nitrous oxide; nitrogen dioxide; water vapor; hydrogen peroxide; and mixtures thereof;
- the metal containing film comprises nitrogen, and the reactant is at least one member selected from: nitrogen; ammonia; hydrazine; alkyl derivatives; nitrogen containing radicals (e.g. N., NH., or $NH_2$.); nitric oxide; nitrous oxide; nitrogen dioxide; amines; and mixtures thereof;
- the metal containing film comprises carbon, and the reactant is at least one member selected from: methane; ethane; propane; butane; ethylene; propylene; tert-butylene; isobutylene; carbon tetrachloride; and mixtures thereof;
- the metal containing film comprises silicon, and the reactant is at least one member selected from: $SiH_4$; $Si_2H_6$; $Si_3H_8$; a $Si(NR^1R^2)_4$ wherein $R^1$ and $R^2$ are independently selected from H or a linear, branched or cyclic C1-C6 alkyl group; $(SiH_3)_3N$; $(SiH_3)_2O$; an alkoxysilane of the general formula $SiH_x(OR^1)_{4-x}$, where x is an integer ranging from 0 to 4 inclusive, and $R^1$ is independently selected from H or a linear, branched or cyclic C1-C6 alkyl group; a silanol of the general formula $Si(OH)_x(OR^1)_{4-x}$, where x is an integer ranging from 0 to 4 inclusive, and $R^1$ is independently selected from H or a linear, branched or cyclic C1-C6 alkyl group; an aminosilane of the general formula $SiH_x(NR^1R^2)_{4-x}$, where x is an integer ranging from 0 to 4 inclusive, and $R^1$ and $R^2$ are independently selected from H or a linear, branched or cyclic C1-C6 alkyl group; and mixtures thereof;
- the metal containing film comprises germanium, and the reactant is at least one member selected from: $GeH_4$; $Ge_2H_6$; $Ge_3H_8$; a $Ge(NR^1R^2)_4$ wherein $R^1$ and $R^2$ are independently selected from H or a linear, branched or cyclic C1-C6 alkyl group; (GeH$_3$)$_3$N; (GeH$_3$)$_2$O; an alkoxy germane of the general formula GeH$_x$(OR$^1$)$_{4-x}$, where x is an integer ranging from 0 to 4 inclusive, and R$^1$ is independently selected from H or a linear, branched or cyclic C1-C6 alkyl group; a germanol of the general formula Ge(OH)$_x$(OR$^1$)$_{4-x}$ where x is an integer ranging from 0 to 4 inclusive, and R$^1$ is independently selected from H or a linear, branched or cyclic C1-C6 alkyl group; an aminogermane of the general formula GeH$_x$(NR$^1$R$^2$)$_{4-x}$, where x is an integer ranging from 0 to 4 inclusive, and R$^1$ and R$^2$ are independently selected from H or a linear, branched or cyclic C1-C6 alkyl group; and mixtures thereof;

the reactant is at least one member selected from: Si(OH)(OtBu)$_3$; SiH(NMe$_2$)$_3$; SiH$_2$(NHtBu)$_2$; and SiH$_2$(NEt$_2$)$_2$;

the reactant is at least one member selected from: Ge(OH)(OtBu)$_3$; GeH(NMe$_2$)$_3$; GeH$_2$(NHtBu)$_2$; and GeH$_2$(NEt$_2$)$_2$;

the precursor and the reactant are introduced into the reaction chamber simultaneously, in keeping with a chemical vapor type deposition ("CVD") process;

the precursor and the reactant are introduced into the reaction chamber sequentially, in keeping with an atomic layer type deposition ("ALD") process;

the precursor and the reactant are mixed together and introduced into the reaction chamber as a mixture;

the precursor and the reactant are pulsed into the reaction chamber;

the reactant is decomposed to its radical form, prior to its introduction into the reactant chamber, by passing the reactant through a remotely located plasma system;

the precursor has a melting point less than or equal to about 80° C., preferably less than or equal to about 35° C.;

the substrate is maintained at a temperature between about 150° C. and about 350° C.;

the precursor has a vapor pressure greater than about 0.1 torr at about 130° C.; and the precursor is selected from: Ni(pda)$_2$; Ni(dmpda)$_2$; Ni(depda)$_2$; Ni(diPrpda)$_2$; Co(pda)$_2$; Co(dmpda)$_2$; Co(depda)$_2$; and Co(diPrpda).

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

Notation and Nomenclature

Certain terms are used throughout the following description and claims to refer to various components and constituents. This document does not intend to distinguish between components that differ in name but not function.

As used herein, the term "alkyl group" refers to saturated functional groups containing exclusively carbon and hydrogen atoms. Further, the term "alkyl group" may refer to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the abbreviation, "Me," refers to a methyl group; the abbreviation, "Et," refers to an ethyl group; the abbreviation, "t-Bu," refers to a tertiary butyl group; the abbreviation, "pda", refers to pentane-2,4,-diketiminato; the abbreviation, "dmpda", refers to N,N'-dimethyl-pentane-2,4-diketiminato; the abbreviation, "depda", refers to N,N'-diethyl-pentane-2,4-diketiminato; the abbreviation, "diPrpda", refers to N,N'-di-isopropyl-pentane-2,4-diketiminato.

As used herein, the term "independently" when used in the context of describing R groups should be understood to denote that the subject R group is not only independently selected relative to other R groups bearing different superscripts, but is also independently selected relative to any additional species of that same R group. For example in the formula GeR$^1$$_x$(NR$^2$R$^3$)$_{(4-x)}$, where x is 2 or 3, the two or three R$^1$ groups may, but need not be identical to each other or to R$^2$ or to R$^3$. Further, it should be understood that unless specifically stated otherwise, values of R groups are independent of each other when used in different formulas.

DESCRIPTION OF PREFERRED EMBODIMENTS

In an embodiment, a method for depositing a metal containing thin film on a substrate comprises introducing a vapor phase metal-organic precursor into a reaction chamber containing one or more substrates. The precursor has at least one β-diketiminato ligand, and has the general formula:

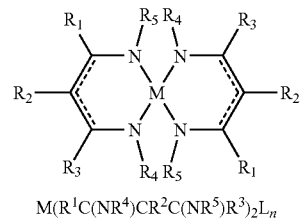

M(R$^1$C(NR$^4$)CR$^2$C(NR$^5$)R$^3$)$_2$L$_n$ wherein M is a metal selected from nickel, cobalt, ruthenium, iridium, palladium, platinum, silver and gold. Each of R$^{1-5}$ is an organic ligand independently selected from H; and a C$_1$-C$_4$ linear or branched, alky group, alkylsilyl group, alkylamide group, alkoxide group, or alkylsilylamide group. Each L is independently selected from: a hydrocarbon; an oxygen-containing hydrocarbon; an amine; a polyamine; a bipyridine; an oxygen containing heterocycle; a nitrogen containing heterocycle; and combinations thereof; and n is an integer ranging from 0 to 4, inclusive.

Generally, the disclosed precursors have a low melting point. In at least one embodiment, the precursor has a melting point lower than about 80° C., alternately less than about 35° C. In some embodiments, the vapor pressure of the precursor is greater than 0.1 torr at about 130° C.

The disclosed precursor compounds may be deposited using any deposition methods known to those of skill in the art. Examples of suitable deposition methods include without limitation, conventional CVD, low pressure chemical vapor deposition (LPCVD), atomic layer deposition (ALD), pulsed chemical vapor deposition (P-CVD), plasma enhanced atomic layer deposition (PE-ALD), or combinations thereof. In an embodiment, the precursor may be introduced into a reaction chamber in a vapor phase. The reaction chamber may be any enclosure or chamber within a device in which deposition methods take place such as without limitation, a cold-wall type reactor, a hot-wall type reactor, a single-wafer reactor, a multi-wafer reactor, or other types of deposition systems under conditions suitable to cause the precursors to react and form the layers. The precursor may be introduced into the reaction chamber by bubbling an inert gas (e.g. $N_2$, He, Ar, etc.) into the precursor and providing the inert gas plus vapor phase precursor mixture to the reactor. In another embodiment, the precursor may be fed to a vaporizer as a liquid, where it is vaporized. The liquid precursor may be mixed with a solvent or a stabilizer (e.g. octane, hexane, pentane, tetramethylsilane, etc). The concepts of vaporization and bubbling would be generally understood by one of skill in the art.

Generally, the reaction chamber contains one or more substrates on to which the metal layers or films will be deposited. The one or more substrates may be any suitable substrate used in semiconductor manufacturing. Examples of suitable substrates include without limitation, silicon substrates, silica substrates, silicon nitride substrates, silicon oxy nitride substrates, tungsten substrates, or combinations thereof. Additionally, substrates comprising tungsten or noble metals (e.g. platinum, palladium, rhodium or gold) may be used.

In some embodiments, one or more reactants are also introduced into the reaction chamber. The selection of the type of reactant may affect the properties of the metal film which is deposited on the substrate. For instance, if the reactant contains oxygen, nitrogen, silicon, carbon, or germanium, then the resultant film may also contain these (alone, or in combination) along with the metal. Some examples of possible films include, but are not limited to, the following types of films: MN, MC, MO, MSi, MSiN, MSiON, MGe; $M^1M^2O_xN_y$, and $MO_xN_y$.

In embodiments, the reaction chamber may be maintained at a pressure ranging from about 1 mtorr to about 100 torr, alternatively from about 1 torr to about 10 torr. In addition, the temperature within the reaction chamber may range from about 100° C. to about 500° C., alternatively from about 120° C. to about 450° C., alternatively from about 150° C. to about 350° C.

The precursor and any optional reactants may be introduced sequentially (as in ALD) or simultaneously (as in CVD) into the reaction chamber. In some embodiments, the reaction chamber is purged with an inert gas between the introduction of the precursor and the introduction of the reactant. In one embodiment, the reactant and the precursor may be mixed together to form a reactant/precursor mixture, and then introduced to the reactor in mixture form. In some embodiments, the reactant may be treated by a plasma, in order to decompose the reactant into its radical form. In these embodiments, the plasma is generally at a location removed from the reaction chamber, for instance, in a remotely located plasma system. One of skill in the art would generally recognize methods and apparatus suitable for such plasma treatment.

In one embodiment, the precursor and the reactant may be pulsed sequentially or simultaneously (e.g. pulsed CVD) into the reaction chamber while reactant gas is introduced continuously into the reaction chamber. Each pulse of the precursor and reactant may last for a time period ranging from about 0.01 s to about 10 s, alternatively from about 0.3 s to about 3 s, alternatively from about 0.5 s to about 2 s. In another embodiment, an inert gas may also be pulsed into the reaction chamber. In such embodiments, the pulse of each gas may last for a time period ranging from about 0.01 s to about 10 s, alternatively from about 0.3 s to about 3 s, alternatively from about 0.5 s to about 2 s.

EXAMPLES

The following non-limiting examples are provided to further illustrate embodiments of the invention. However, the examples are not intended to be all inclusive and are not intended to limit the scope of the inventions described herein.

Example 1

Prophetic Atomic Layer Deposition of Ni Thin Films Using Ni(pda)$_2$

Ni(pda)$_2$ is introduced into a container. The container is heated at 90° C. and $N_2$ is used as carrier gas at a flow of 50 sccm. The pressure the container is controlled at 50 Torr. $H_2$ is used as a reducing agent. The substrate is heated at 350° C. During a first step, Ni(pda)$_2$ is introduced into the reaction chamber during 2 s. A $N_2$ purge of 5 s is performed afterwards as second step. As third step, a pulse of $H_2$ is then introduced into the reaction chamber during 2 s, followed by a 2 s $N_2$ purge as fourth step. All four steps are repeated 100 times to obtain a Ni film. Self-limited atomic layer deposition is thus obtained. Similar experiments with similar results can be expected with $NH_3$ as the reducing agent.

Example 2

Prophetic Metal-Organic Chemical Vapor Deposition of NiO Using Ni(pda)$_2$

Ni(pda)$_2$ is introduced into a container. The container is heated at 90° C. and $N_2$ is used as carrier gas at a flow of 50 sccm. The pressure in the container is controlled at 50 Torr. Ni(pda)$_2$ is mixed to a $O_2/N_2$ gas mixture into the reaction chamber. The substrate is heated at 350° C. The pressure inside the reaction chamber is set at 10 Torr. A film of nickel oxide is obtained. Similar experiments results can be expected with late transition metal series analogs.

While embodiments of this invention have been shown and described, modifications thereof can be made by one skilled in the art without departing from the spirit or teaching of this invention. The embodiments described herein are exemplary only and not limiting. Many variations and modifications of the composition and method are possible and within the scope of the invention. Accordingly the scope of protection is not limited to the embodiments described herein, but is only limited by the claims which follow, the scope of which shall include all equivalents of the subject matter of the claims.

What is claimed is:
1. A method for depositing a metal containing thin film on a substrate; comprising:
   a) introducing a vapor phase metal-organic precursor into a reaction chamber containing one or more substrates, wherein the precursor comprises a compound with at least one β-diketiminato ligand, and which has the general formula:

$M(R^1C(NR^4)CR^2C(NR^5)R^3)_2L_n$ wherein:
   M is a metal selected from the group consisting of: nickel, cobalt, ruthenium, iridium, palladium, platinum, silver and gold;

each of $R^{1-5}$ is an organic ligand independently selected from the group consisting of: H; and a $C_1$-$C_4$ linear or branched, alky group, alkylsilyl group, alkylamide group, alkoxide group, or alkylsilylamide group;

each L is independently selected from the group consisting of: a hydrocarbon; an oxygen-containing hydrocarbon; an amine; a polyamine; a bipyridine; an oxygen containing heterocycle; a nitrogen containing heterocycle; and combinations thereof; and n is an integer ranging from 0 to 4, inclusive;

b) depositing a metal containing film onto the substrate, wherein the substrate is maintained at a temperature between about 100° C. and about 500° C.

2. The method of claim 1, further comprising introducing at least one reactant into the reaction chamber.

3. The method of claim 2, wherein the metal containing film comprises oxygen, and wherein the reactant comprises at least one member selected from the group consisting of: oxygen; oxygen radicals (e.g. O. or OH.); ozone; nitric oxide; nitrous oxide; nitrogen dioxide; water vapor; hydrogen peroxide; and mixtures thereof.

4. The method of claim 2, further comprising introducing the precursor and the reactant into the reaction chamber sequentially.

5. The method of claim 1, wherein the precursor has a melting point less than or equal to about 80° C.

6. The method of claim 5, wherein the precursor has a melting point less than or equal to about 35° C.

7. The method of claim 1, wherein the substrate is maintained at a temperature between about 150° C. and about 350° C.

8. The method of claim 1, wherein the precursor has a vapor pressure greater than about 0.1 torr at about 130° C.

* * * * *